United States Patent
Tapia Limonchi et al.

(10) Patent No.: US 12,123,017 B2
(45) Date of Patent: Oct. 22, 2024

(54) COMPOSITION AND METHOD FOR CULTIVATION, EXPANSION, PRESERVATION AND/OR CELL PRETREATMENT

(71) Applicant: REGENERO S.A., Santiago (CL)

(72) Inventors: Rafael Tapia Limonchi, Santiago (CL); Maroun Khoury, Santiago (CL); Daniel Meza Rojas, Santiago (CL)

(73) Assignee: REGENERO S.A., Santiago (CL)

( * ) Notice: Subject to any disclaimer, the term of this patent is extended or adjusted under 35 U.S.C. 154(b) by 952 days.

(21) Appl. No.: 16/767,383

(22) PCT Filed: Nov. 27, 2017

(86) PCT No.: PCT/CL2017/050070
§ 371 (c)(1),
(2) Date: May 27, 2020

(87) PCT Pub. No.: WO2019/100175
PCT Pub. Date: May 31, 2019

(65) Prior Publication Data
US 2020/0385671 A1     Dec. 10, 2020

(51) Int. Cl.
| | | |
|---|---|---|
| C12N 5/00 | (2006.01) | |
| C12N 5/073 | (2010.01) | |
| C12N 5/074 | (2010.01) | |
| C12N 5/0775 | (2010.01) | |
| C12N 5/0783 | (2010.01) | |
| C12N 5/0784 | (2010.01) | |

(52) U.S. Cl.
CPC ......... *C12N 5/0043* (2013.01); *C12N 5/0037* (2013.01); *C12N 5/0056* (2013.01); *C12N 5/0603* (2013.01); *C12N 5/0637* (2013.01); *C12N 5/0639* (2013.01); *C12N 5/0662* (2013.01); *C12N 5/0696* (2013.01); *C12N 2500/22* (2013.01); *C12N 2500/30* (2013.01)

(58) Field of Classification Search
None
See application file for complete search history.

(56) References Cited

U.S. PATENT DOCUMENTS

| | | |
|---|---|---|
| 2017/0165194 A1 | 6/2017 | Meng et al. |
| 2017/0175080 A1 | 6/2017 | Barlow et al. |

FOREIGN PATENT DOCUMENTS

| | | | | |
|---|---|---|---|---|
| CN | 102433302 | | 5/2012 | |
| CN | 102433302 A | * | 5/2012 | |
| WO | WO-2017012774 A1 | * | 1/2017 | ............ A61K 31/09 |

OTHER PUBLICATIONS

Hai et al. Serum-free culture medium for mesenchymal stem cells (2012) CN102433302 A, Espacenet English Translation. (Year: 2012).*
Thermo Fisher Scientific, DMEM/F-12, www.thermofisher.com, Accessed May 2, 2023. (Year: 2023).*
Lener et al. Applying extracellular vesicles based therapeutics in clinical trials—an ISEV position paper (2015), Jorunal of Extracellular Vesicles, 4, pp. 1-31 (Year: 2015).*
Corwin et al. Characterization and modulation of human mesenchymal stem cell stress pathway response following hypothermic storage (2014), Cryobiology, 68, pp. 215-226. (Year: 2014).*
Astori, et al., "Platelet lysate as a substitute for animal serum for the ex-vivo expansion of mesenchymal stem/stromal cells: present and future", Stem Cell Research & Therapy, 2016, vol. 7, No. 1, pp. 1-8.
Fischer-Valuck, et al., "Migratory response of mesenchymal stem cells to macrophage migration inhibitory factor and ts antagonist as a function of colony-forming efficiency", Biotechnology Letters, 2010, vol. 32, pp. 19-27.
Bloom, et al., "Identification of iguratimod as an inhibitor of macrophage migration inhibitory factor (MIF) with steroid-sparing potential", Journal of Biological Chemistry, 2016, vol. 291, No. 51, pp. 26502-26514.
Lee, et al., Blueberry isolate, pterostibene, functions as a potential anticancer stem cell agent in suppressing rradiation-mediated enrichment of hepatoma stem cells, Evidence-based Complementary and Alternative Medicine, 2013, vol. 2013, pp. 1-9.
Simpson, et al., "Macrophage migration inhibitory factor promotes tumor growth and metastasis by inducing myeloie-derived suppressor cells in the tumor microenvironment", The Journal of Immonology, 2012, vol. 189, No. 12, pp. 5533-5540.
Laitinen, et al., "A robust and reproducible animal serum-free culture method for clinical-grade bone marrow-derived mesenchymal stromal cells", Cytotechnology, 2016, vol. 68, pp. 891-906.
Capelli, et al., "Human platelet lysate allows expansion and clinical grade production of mesenchymal stromal cells from small samples of bone marrow aspirates or marrow filter washouts", Bone Marrow Transplantation, 2007, vol. 40, pp. 785-791.
Riordan, et al. "Scalable efficient expansion of mesenchymal stem cells in xeno free media using commercially available reagents", J Transl Med 13, 232 (2015).
Burnouf, et al., "Human platelet lysate: Replacing fetal bovine serum as a gold standard for human cell propagation?", Biomaterials, vol. 76, 2016, pp. 371-387.
Golebiewska, et al. "Platelet secretion: From haemostasis to wound healing and beyond", Blood reviews, 2015, 29(3), 153-162.
Nurden, et al., "Platelets and wound healing", Front Biosci. 2008;13:3532-3548.
Pirkmajer, et al., "Serum starvation: caveat emptor", Am J Physiol Cell Physiol.. 2011; 301(2):C272-9.
Szekeres, et al., "Resveratrol and Resveratrol Analogues—Structure—Activity Relationship", Pharm Res 27, 1042-1048 (2010).

(Continued)

*Primary Examiner* — Kara D Johnson
*Assistant Examiner* — Maytee Marie Contes De Jesus
(74) *Attorney, Agent, or Firm* — Merchant & Gould P.C.

(57) ABSTRACT

The invention relates to a method and composition for the cultivation, expansion and production of extracellular vesicles, and the preservation and/or pre-treatment of cells, wherein said composition is a medium or media supplement or a solution comprising pterostilbene or the derivatives thereof, and/or a migration inhibitory factor antagonist and optionally a bivalent cation.

16 Claims, 7 Drawing Sheets

(56) References Cited

OTHER PUBLICATIONS

Sun, et al. "Serum deprivation elevates the levels of microvesicles with different size distributions and selectively enriched proteins in human myeloma cells in vitro", Acta pharmacologica Sinica, 2014, 35(3), 381-393.
International Search Report issued in International Application No. PCT/CL2017/050070, Jun. 18, 2018, 8 pages.

* cited by examiner

| Samples | Total particles<br>Medium of the invention SF/XF | Total particles<br>Commercial solution FBS, post induction |
|---|---|---|
| D5 | 1.98E+09 | --- |
| D8 | 1.08E+10 | 2.17E+09 |
| D12 | 1.83E+10 | 9.62E+09 |
| Total | 3.11E+10 | 1.18E+10 |

Yield of particles from commercial solution vs medium of the invention, D12

COMPOSITION AND METHOD FOR CULTIVATION, EXPANSION, PRESERVATION AND/OR CELL PRETREATMENT

FIELD OF THE INVENTION

The invention relates to the general field of biotechnology, and specifically relates to the field of regenerative medicine and the manufacture of therapy products based on human cells (HCT/Ps). This invention comprises a composition for the culture, expansion, preservation of cells and/or pretreatment of cells where said composition is a medium, medium supplement and/or solution comprising pterostilbene, an antagonist of the migration inhibitory factor and a bivalent cation in combination or by separated.

STATE OF THE ART

Currently, cell therapy is a bridge between translational research and clinical research and constitutes an advance regarding tissue engineering in order to replace, regenerate and/or modify human cells, tissues or organs in order to regain functionality. This translation is accompanied and encouraged by an increasing number of clinical trials using stem cells, mainly mesenchymal stem cells (MSC). Although the field of cell therapy has advanced rapidly in various medical applications, in its development there are various technical problems that require better solutions, which allow, on the one hand, to lower the costs of these technologies, and also make them more efficient and safe, in a way to be able to help more people and in new applications, Below we will describe some of the problems that persist in the current technique that can be solved or diminished with the medium, medium supplement or solution for the cultivation, expansion, preservation of cells and/or pretreatment of cells of the invention.

So far, most clinical trials have used MSCs grown in media containing fetal bovine serum (FBS). These tests require a considerable number of cells and in order to avoid complications associated with FBS (risk of transmission of xenogenic infectious agents and immunization), the use of alternative supplements or serum free culture media (serum free), and even more free of animal components (xeno free) is preferable and highly recommended by agents regulators [1].

Numerous groups have developed serum-free culture media compositions for the growth and expansion of MSC. Platelet-derived growth factor (PDGF) is a potent cellular mitogen and has been reported to be a significant component of FBS that enables cell proliferation in vitro [2-5]. In this context, human platelet lysate (hPL) has been established as a suitable alternative to fetal bovine serum as a supplement to culture media, enabling efficient proliferation of human stem cells under serum free conditions (SF) in the context of cell therapy and tissue engineering. Platelets store a number of bioactive mediators, including chemokines and growth factors, such as PDGF, transforming growth factor beta (TGF-β), insulin-like growth factor-1 (IGF-1), vascular growth factor (VEGF), epidermal growth factor (EGF), among others [5-7]. Despite the described advantages, its use has some associated disadvantages, for example anticoagulants should be used together with heparin to prevent gelatinization of the media and variations in concentrations of the growth factors that they possess, additionally a major disadvantage is the low availability of batches of platelets to consider it as a consistent and scalable culture medium supplement. Therefore, it is desirable in the art to find alternatives to replace, or at least decrease, their use in the culture media.

On the other hand, some vesicles secreted by cells during cell culture have great potential to constitute cell-free therapies. The role of exosomes has been studied in various fields, among them it has been found that they play an important role in intercellular communication, that they have an effect on the formation and/or modulation of diseases through the content of the exosome and, finally, exosomes have been used as vehicles for the delivery of different drugs. It is for these reasons that the development of therapies based on exosomes and extracellular vesicles has advances in preclinical studies and great potential for clinical application. However, for their production the cells are frequently cultured in media supplemented with FBS containing inherent vesicles of bovine fetal origin, and which may potentially interfere with the therapeutic effect. To avoid this contamination with vesicles of bovine origin, a common method used in the prior art is the culture of cells with serum deprivation, a method that allows to collect the vesicles directly from the culture media, however, this culture constitutes an environmental stress for the cells, which reduces basal cell activity and induces apoptosis in some cells [6,7 and 9]. Therefore, for clinical use, efficient ex-vivo expansion of cells (MSCs, SCs, lymphocytes, or others) in a serum free/xeno free medium that does not subject cells to environmental stress is a challenging requirement for a robust production, large-scale and cost-effective extracellular cells and products, such as extracellular vesicles, of clinical grade.

For these reasons, serum-free and better still free of animal components (xeno free) culture conditions must be able to support the isolation and rapid expansion of different cell types, to produce large numbers of pure, clinically grade cells and exosomes for cell therapy and cell-free therapies for different diseases.

Furthermore, with the advances in regenerative medicine and cell therapy, there is also a need for adequate storage of cellular and biological products in order to preserve to the maximum the biological properties. In this sense, the technologies of cryopreservation (storage at ultra low temperatures) and biopreservation (hypothermic storage) have emerged as a long-term viable option for safe transportation within short periods and distances.

The design of preservation solutions (cryo or bio) that allow high survival cell rates compatible with maintaining the biological properties of cells is a great challenge for the cell therapy (CT) industry. Currently, many of cryoprotective agents (CPAs) used to protect cell structures during cooling and thawing processes are not efficient enough or are not compatible with clinical use. Dimethyl sulfoxide (DMSO) is an intracellular CPA used to protect cellular structures during the cooling process, but its clinical use is currently under discussion for its toxicity. Therefore, developing serum-free and/or xeno-free cryopreservation solutions (depending on the application the cells will be used) that combine low percentages of CPAs (or no CPAs) with inhibitors of refrigeration-induced cell death are presented as a technical problem to solve, to obtain a cryopreserved cellular product "ready to use" in cellular therapies.

In another aspect, it is widely described that oxidative stress can affect longevity and cell functionality. In different cell types, including MSCs, the conditions culture and ex vivo expansion produce metabolic changes to cells that can generate activation of oxidative stress signals, produced by the generation of reactive oxygen species (ROS) or reactive nitrogen species (RNS). For example, in MSCs, an increase in ROS concentration inhibits cell proliferation, increases senescence, affects the differentiation potential of MSCs, as well as inhibits immunomodulation in this cell type. Consequently, ex vivo expansion is dramatically reduced and likewise affects the genomic stability of cells after multiple passages. The use of culture media or antioxidant agents that can counteract the effect of ROS and oxidative stress on MSCs and other cell types, keeping stable the functionality and genomic stability can be appropriately used for productive scaling procedures of cell cultures.

In this context, the invention described here solves all these technical problems, providing a medium, medium supplement and solution for cell culture, expansion, preservation and/or pretreatment, wherein the medium, medium supplement and solution comprises pterostilbene and/or migration inhibitory factor antagonists and/or a bivalent cation in combination or separately, as a culture medium, supplement of culture medium or solution to enhance cell culture, cell expansion, cell preservation and obtaining extracellular products. These molecules can also be used for pretreatment of cells that will be exposed to highly oxidative environments according to the methodsand compositions of the invention described below. The method and means described in this document would contribute greatly to the realization of culture protocols or solutions enhanced to meet efficacy criteria in upcoming clinical studies and cell therapy procedures.

Pterostilbene is an antioxidant molecule of stilbene's family, it is analogous to resveratrol, and is derived from small berries such as blueberries and grapes [8]. This compound is used as a therapeutic agent, in particular for the treatment and/or prevention of cancer. For example, WO2017012774 (A1) describes a combination comprising pterostilbene or pterostilbene phosphate or a pharmaceutically acceptable salt thereof, a glutathione-removing agent and a chemotherapeutic agent for this effect.

Cell migration factor antagonists are chosen from ISO-1, ISO-66, ISO-92 p425, K664-1, K-647, K-679, K-680, K-664.1, OXIM-11, D-T4, T-614 or Iguratimod. In a preferred embodiment, ISO-1 is used, or also known as migration inhibitor factor (MIF) antagonist, it is an inhibitor of cytokine D-dopachrome tautomerase (D-DT) activity in vitro and in cells. It blocks the activation of NF-κβ and TNF-α secretion from LPS-treated macrophages. The MIF antagonist is usually used to improve the survival of mice that present sepsis, it demonstrates protective effects in their respiratory tract and in their gastrointestinal inflammation.

The bivalent cations that can optionally be added to the medium of the invention are chosen from zinc ion ($Zn^{+2}$), beryllium ion ($Be^{+2}$), cadmium ion ($Cd^{+2}$), magnesium ion ($Mg^{+2}$), copper (II) ion (cupric, $Cu^{+2}$), calcium ion ($Ca^{+2}$), nickel (II) ion (nickel, $Ni^{+2}$), lead (II) ion (plumbose, $Pb^{+2}$), (II) tin ion (stannous, $Sn^{+2}$), mercury ion (II) (mercuric, $Hg^{+2}$), cobalt (II) ion (cobalt, $Co^{+2}$), iron (II) ion (ferrous, $Fe^{+2}$), manganese (II) ion (manganous, $Mn^{+2}$), barium ion ($Ba^{+2}$), strontium ion ($Sr^{+2}$), chromium (II) ion ($Cr^{+2}$), strontium ion ($Sr^{+2}$), radio ion ($Ra^{+2}$). In a preferred embodiment, Zn is used as a bivalent cation, classical media usually does not contain $Zn^{+2}$ in their basal formulations. Currently its application for cryo and/or biopreservation has not been described.

REFERENCES

1. Laitinen, A., Oja, S., Kilpinen, L., Kaartinen, T., Möller, J., Laitinen, S., Korhonen, M., & Nystedt, J. (2016). A robust and reproducible animal serum-free culture method for clinical-grade bone marrow-derived mesenchymal stromal cells. *Cytotechnology,* 68(4), 891-906. doi.org/10.1007/s10616-014-9841-x
2. Capelli, C., Domenghini, M., Borleri, G. et al. Human platelet lysate allows expansion and clinical grade production of mesenchymal stromal cells from small samples of bone marrow aspirates or marrow filter washouts. Bone *Marrow Transplant* 40, 785-791 (2007). doi.org/10.1038/sj.bmt.1705798
3. Riordan, N. H., Madrigal, M., Reneau, J. et al. Scalable efficient expansion of mesenchymal stem cells in xeno free media using commercially available reagents. *J Transl Med* 13, 232 (2015). doi.org/10.1186/s12967-015-0561-6
4. Thierry Burnouf, Dirk Strunk, Mickey B. C. Koh, Katharina Schallmoser, Human platelet lysate: Replacing fetal bovine serum as a gold standard for human cell propagation?, Biomaterials, Volume 76, 2016, Pages 371-387, ISSN 0142-9612, doi.org/10.1016/j.biomaterials.2015.10.065.
5. Golebiewska, E. M., & Poole, A. W. (2015). Platelet secretion: From haemostasis to wound healing and beyond. *Blood reviews,* 29(3), 153-162. doi.org/10.1016/j.blre.2014.10.003
6. Nurden A T, Nurden P, Sanchez M, Andia I, Anitua E. Platelets and wound healing. Front Biosci. 2008; 13:3532-3548
7. Pirkmajer S, Chibalin AV. Serum starvation: caveat emptor. Am J Physiol Cell Physiol. 2011 August; 301(2): C272-9. doi: 10.1152/ajpcell.00091.2011.
8. Szekeres, T., Fritzer-Szekeres, M., Saiko, P. et al. Resveratrol and Resveratrol Analogues—Structure—Activity Relationship. *Pharm Res* 27, 1042-1048 (2010). doi.org/10.1007/s11095-010-0090-1
9. Sun, L., Wang, H. X., Zhu, X. J., Wu, P. H., Chen, W. Q., Zou, P., Li, Q. B., & Chen, Z. C. (2014). Serum deprivation elevates the levels of microvesicles with different size distributions and selectively enriched proteins in human myeloma cells in vitro. *Acta pharmacologica Sinica,* 35(3), 381-393. doi.org/10.1038/aps.2013.166

BRIEF DESCRIPTION OF THE INVENTION

In one aspect, the present invention provides a composition for culturing, expanding, preserving, pre-treating cells, and/or obtaining extracellular products, where said composition is a medium or medium supplement or solution. The present invention relates to a composition comprising at least pterostilbene or derivatives thereof, and/or a migration factor antagonist and optionally a bivalent cation.

In one embodiment, the invention relates to a culture medium or culture medium supplement for the culture and/or expansion of cells, characterized by being serum-free and/or free of animal agents, comprising pterostilbene or derivatives thereof and/or a migration factor antagonist and optionally a bivalent cation.

In another embodiment, the invention relates to a method of producing extracellular vesicles (VEs), including exosomes, wherein the cells are preferably cultured in a serum-free medium of the invention and the exosomes and/or extracellular vesicles are collected by methods known in the art. In a second aspect, the present invention relates to a solution, which corresponds to a clinical grade solution for the preservation of cells. Said solution is characterized by being serum-free and/or free of animal agents, comprising pterostilbene or derivatives thereof and/or a migration factor antagonist and optionally a bivalent cation.

In another embodiment, the invention relates to a solution for preserving cells, and a method for preserving cells, which comprises contacting the cells with a solution of the invention comprising pterostilbene or derivatives thereof, an antagonist of migration inhibiting factor and a bivalent cation in combination or separately.

In a third aspect, the invention relates to a medium or medium supplement that it comprises pterostilbene or derivatives thereof, a migration inhibitory factor antagonist and a bivalent cation in combination or separately. Wherein the medium is a culture medium, a serum free culture medium, a culture medium free of animal components, or a clinical grade solution for cell pretreatment. In a second embodiment, the invention provides the method for the pretreatment of cells to improve the conditions of cultures that will be subjected to oxidative and/or oxidative stress conditions.

Finally, the invention relates to a method for growing, expanding, preserving and/or pretreating cells where cells are grown, expanded, preserved or pre-treated in contact with a culture medium, medium supplement or solution comprising pterostilbene or its derivatives, and/or a migration inhibitory factor antagonist and optionally a bivalent cation.

DESCRIPTION OF THE FIGURES

FIG. 1A. Accumulated population after 3 passages of umbilical cord MSCs measured by cell exclusion test for trypan blue proliferation cultured in DMEM/F12 supplemented with 25 µg/L bFGF, 2 µg/L TGFβ, 2% human platelet lysate and nanomolar concentrations of pterostilbene (F1:100 nM, F2:250 nM, F3:500 nM F4:up to 1000 nM). FIG. 1B. Morphological analysis of umbilical cord MSCs cultured in DMEM/F12 supplemented with 25 µg/L bFGF, 2 µg/L TGFβ, 2% human platelet lysate and nanomolar concentrations of pterostilbene (from F1 to F4, 100 nM at 1000 nM, respectively). FIG. 1C. Analysis of identity and purity markers through flow cytometry of the characteristic markers of MSC: CD105, CD90, CD75, CD45, CD34, CD19, CD14 and HLA-DR. FIG. 1D. Analysis of the MSC tri-differentiation potential, the cells maintain their tridifferentiation potential. FBS: fetal bovine serum, Ptsb: Pterostilbene, hPL: human platelet lysate.

FIG. 2A. Accumulated population after 3 passages of umbilical cord MSCs measured by exclusion test for trypan blue cell proliferation cultured in DMEM/F12 supplemented with 25 µg/L bFGF, 2 µg/L TGFβ and nanomolar concentrations of pterostilbene (F1:100 nM, F2:250 nM, F3:500 nM F4: up to 1000 nM). FIG. 2B. Morphological analysis of umbilical cord MSCs cultured in DMEM/F12 supplemented with 25 µg/L of bFGF, TGFβ 2 µg/L and nanomolar concentrations of pterostilbene (F1:100 nM, F2:250 nM, F3:500 nM F4: up to 1000 nM), shows that the cultures in the presence of antioxidants are more confluent than the control condition and in the absence of Pterostilbene, they also retain the typical fibroblast morphology of MSC (FIG. 2B). FBS: Bovine Fetal Serum, Ptsb: Pterostilbene, hPL: Human Platelet Lysate.

Production of exosomes in culture medium of the invention SF/XF, free of platelets, allows cell culture and proliferation, allowing sustained production of extracellular vesicles, without subjecting cells to metabolic changes. FIG. 3A. Quantification of particles obtained from supernatant from 3D MSC cell cultures, on days 5, 8 and 12 in the culture medium of the invention and by cultivation with commercial culture medium and FBS, by induction. FIG. 3B. 3D yield of extracellular vesicles culture of mesenchymal stem cells. Total particles and extracellular vesicles smaller than 150 nm were quantified. The sustained culture of the invention allows the enrichment of total particles. The medium of the invention SF/XF provides 3.2 times more total particles than the conventional method. Additionally, the culture medium of the invention promotes the production of particles smaller than 150 nm, being 87.7% of the total particles, compared to 14.8% of the total particles obtained with the commercial solution.

FIG. 4A. Mesenchymal stem cells that were preserved with commercial biopreservation solution (CBS) with the addition of the solution of the invention 0.1 µM of Pterostilbene significantly improves the survival of MSCs preserved at 4° C. for 3 days (FIG. 4A). In parallel CBS supplemented with 0.1 µM Pterostilbene and 2.5 µM Zinc, significantly improves the survival of MSCs preserved at 4° C. for 3 days (FIG. 4A). An improvement in the survival of MSCs preserved at 4° C. for 3 days can be observed when using CBS supplemented with 2.5 µM Zinc and 0.1 nM Iso-1, and when using CBS supplemented with 0.1 µM pterostilbene, 2.5 µM Zinc and 0.1 nM Iso-1 (FIG. 4A). FIG. 4B. Cells adherence, after biopreservation with the solution of the invention with Pterostilbene, Zinc and/or ISO-1 compared to the commercial biopreservation solution (CBS), functionally after 3 days of preservation the cells treated with Pterostilbene, zinc and/or ISO-1 are able to adhere better than those cells preserved only with commercial biopreservative (CBS) FIG. 4C. Proliferation after 3 days of cell preservation preserved with CBS versus CBS with addition of the solution of the invention, functionally after 3 days of preservation the cells treated with Pterostilbene can proliferate more efficiently than commercial solution without the supplement of the medium of the invention (FIG. 4C). FIG. 4D. Cells preserved with pterostilbene, Zinc and/or ISO-1 also present higher migration than cells preserved with CBS, and close to fresh cells (FIG. 4D). Pstb: Pterostilbene, CBS: commercial solution for biopreservation.

FIG. 5A. Mesenchymal stem cells were preserved with cryopreservation solution prepared based on human platelets (95%), with 5% cryoprotectant DMSO and supplemented with 2 µM Pterostilbene, this solution improves cell viability with respect to commercial cryopreservative and presents a viability similar to the standard cryopreservation solution (fetal bovine serum and 10% DMSO), (FIG. 5A). FIG. 5B. The effect of Pterostilbene can be verified in FIG. 5B in which the viability is greater in the presence of the antioxidant in the solution of the invention for cryopreservation. FIG. 5C. Similarly, the cryopreservation solution supplemented with 2 µM of Pterostilbene improves post-thaw adherence compared to the standard solution (FIG. 5C). Cryopreservation Solution of the invention [SIC].

DETAILED DESCRIPTION OF THE INVENTION

Figure 1A:
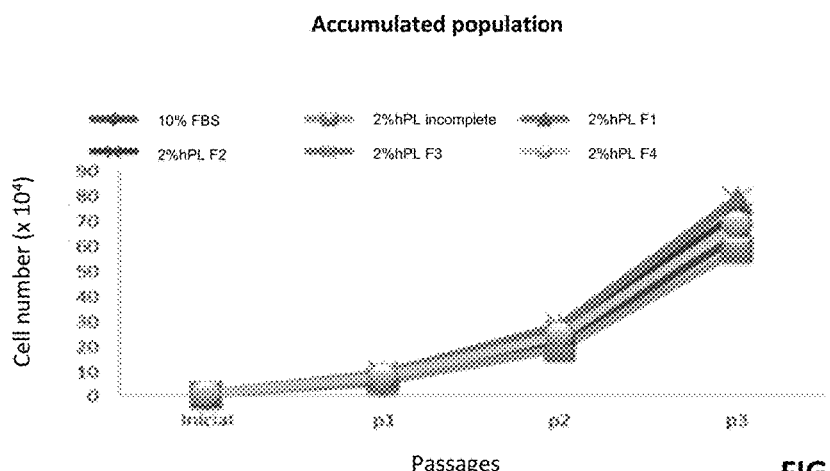
FIGS. 1A-1D. Expansion of MSC in culture medium of the invention with hPL.

The invention is especially related to the field of regenerative medicine and the manufacture of therapy products based on mammalian cells and/or specifically human cells (HCT/Ps), so that in a field of the invention it refers to a composition for cell culture and expansion, obtaining extracellular products, preservation and treatment of cells for the prevention of oxidative stress damage, where said composition is a medium, medium supplement or solution. In a preferred embodiment, the cells to be cultured, expanded, preserved or pretreated are chosen from: dendritic cells, CAR-T cells, T-reg cells, mesenchymal stem cells (MSCs), T lymphocytes, hematopoietic stem cells (HSC), cells pluripotent stem and/or other stem cells (CS) and/or other cell types other than stem cells.

In one aspect, the present invention provides a composition for culturing, expanding, preserving, pretreating cells and/or obtaining extracellular products, wherein said composition is a medium, medium supplement or solution. The present invention relates to a composition comprising at least pterostilbene or derivatives thereof, and/or a migration factor antagonist and optionally a bivalent cation.

In one embodiment, the invention relates to a culture medium or culture medium supplement characterized by being serum-free and/or free of animal agents, comprising pterostilbene or derivatives thereof, and/or a migration factor antagonist and optionally a bivalent cation.

In another embodiment, the invention relates to a method of producing extracellular vesicles (EVs), including exosomes, wherein the cells are preferably cultured in a serum-free medium of the invention and the exosomes and/or extracellular vesicles are collected by methods known in the art.

In a second aspect, the present invention relates to a solution, where said solution corresponds to a clinical grade solution for cell preservation. The solution is characterized by being serum-free and/or free of animal agents, comprising pterostilbene or derivatives thereof and/or a migration factor antagonist and optionally a bivalent cation.

In another embodiment, the invention relates to a method for the cultivation and/or preservation of cells, said method comprising contacting the cells with the medium, medium supplement or solution of the invention comprising pterostilbene or derivatives thereof, migration inhibitory factor antagonist and a bivalent cation in combination or separately Where the method is for the growth and expansion of cells, or for cryopreservation or biopreservation of cells in clinical grade solutions under normal conditions, free of serum or free of animal agents.

In a third aspect, the invention relates to a medium or medium supplement comprising pterostilbene or derivatives thereof, a migration inhibitory factor antagonist and a bivalent cation in combination or separately. Wherein the medium is a culture medium, a serum free culture medium, a culture medium free of animal components, or a clinical grade solution for cell pretreatment. In a second embodiment, the invention provides the method for the pretreatment of cells to improve the conditions of cultures that will be subjected to oxidative and/or oxidative stress conditions.

Definitions

The term "derivatives thereof" refers to any chemical modification of the Pterostilbene molecule or the antagonist of the migration inhibiting factor that does not limit its activity, as well as its pharmaceutically acceptable salts.

The term "pharmaceutically acceptable salt" refers to any pterostilbene or migration inhibiting factor antagonist salt approved by a regulatory agency of the federal or state government or listed in the United States Pharmacopeia or other generally recognized pharmacopoeia for use in animals, and more particularly in humans. Salt preparation can be carried out by methods known in the art. Illustrative non-limiting examples of pharmaceutically acceptable salts include, but are not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartarate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate.

As used herein, the term "culture" refers to any growth of cells, organisms, multicellular entities, or tissue in a medium. The term "cultivating" refers to any method of achieving such growth and may comprise multiple stages.

As used herein, the term "cell culture" refers to an in vitro growth of cells. In such a culture, cells proliferate but are not organized in tissue.

As used herein, the term "culture medium" or "medium" is recognized in the technique, and generally refers to any substance or preparation used for culturing live cells. The term "medium" as such as used in reference to a cell culture, includes the components of the environment surrounding the cells. The media may be solid, liquid, gaseous, or a mixture of phases and materials. The media include liquid growth media as well as media. fluids that do not support cell growth. Media also includes gelatinous media such as agar, agarose, gelatin, and collagen matrices. Examples of gaseous media include the gas phase to which cells are exposed, when grown in a petri dish or other solid or semi-solid support.

As used herein, the term "medium" also refers to material that is intended to be used in cell culture, even if it has not yet been contacted with cells. In other words, a nutrient rich liquid prepared for bacterial culture is a medium. Similarly, a powder mixture that when mixed with water or another liquid becomes suitable for cell culture can be called a "spray medium".

As used herein, the term "basal medium" refers to a medium that promotes the growth of many types of microorganisms and mammalian cells that do not require any special nutritional supplement. Most basal media generally comprise four basic chemical groups: amino acids, carbohydrates, inorganic salts, and vitamins. A basal medium generally serves as the basis for a more complex medium, to which supplements such as serum, buffers, growth factors, lipids, and the like are added. Examples of basal media include, but are not limited to, Eagles Basal Medium, Basal Minimum Medium, Dulbecco's Modified Eagle's Medium (DMEM), HAM-F10 and HAM-F12 Nutrient-Mixed Medium, Mc Coy's 5A, DMEM Medium/F-12, RPMI 1640 and Dulbecco Iscove's Modified Medium (IMDM). In the case of the basal medium for the production of EV and exosomes, the basal medium without phenol red is preferred. Preferably, the basal medium is selected from the list consisting of Eagles' Basal Medium, Basal Minimum Medium, Dulbecco's Modified Eagle's Medium (DMEM), Nutrient-Mixed Medium HAM-F10 and HAM-F12, Mc Coy's 5A, DMEM Medium/F-12, RPMI 1640 and Dulbecco Iscove's Modified Medium (IMDM).

As used herein, the term "supplement for culture medium" refers to a composition that can be added to any culture medium including commercial culture media in order to improve the properties of said culture medium, either for cell culture itself or for expansion, preservation, or pretreatment of cells.

The term "solution" refers to a mixture of different components in a liquid.

The term "growth factor" corresponds to all that substance capable of stimulating cell growth, proliferation and differentiation. There are direct growth factors, that is, they directly affect growth, proliferation and differentiation; as there are also indirect growth factors that maintain cell survival in situations of oxidative stress. For this last situation, the growth factors used in the invention correspond to bFGF, TGF-β.

As referred to herein, "cell culture and expansion method" refers to all those processes for the correct growth and expansion of cells. Which can be in a monolayer or 2D system and/or a suspension culture or 3D. The method of cultivation and expansion in a 3D system includes the use of microcarriers, macrocarriers or beats of different materials, such as dextran, collagen and cellulose with different crosslinks. These include the use of commercial macrocarriers such as BioNOC and Fibra-cell discs, and the use of microcarriers such as Cytodex, Mobius, Hillex CT, Cytopore, and Cytoline.

As used herein, the term "oxidative stress causing situations" refers to those situations in which there is an increase in reactive oxygen species (ROS) and reactive nitrogen species (RNS). ROS are generated during the oxidative metabolism of the mitochondria as well as in response to certain stimuli such as xenobiotic agents, cytokines and bacterial invasion. Oxidative stress refers to an imbalance between the excess of ROS or another oxidant and the capacity of the cell of its antioxidant response. Oxidative stress unleashes damage at the level of macromolecules and is involved in several diseases. Examples of situations that cause oxidative stress are chronic diseases such as atherosclerosis, cancer, diabetes, rheumatoid arthritis, ischemia due to reperfusion, myocardial infarction, cardiovascular diseases, chronic inflammation, stroke and septic shock, aging and other neurodegenerative diseases in humans.

In general, the term "secreted vesicles" refers to the secreted and purified extracellular vesicles (EVs) of most eukaryotic cells. EV are all vesicles released by cells, made up of a lipid bilayer that varies from 50 nm to 1000 nm in diameter depending on their origin and which are generated by the formation of branch in the plasma membrane. In contrast, exosomes, which range from 30 nm to 150 nm, are derived from the endolysosomal pathway.

The term "divalent cation" refers to any cation that has a $+2$ charge. Non-limiting illustrative examples of divalent cations include, but are not limited to $Zn^{+2}$, zinc ion; $Be^{+2}$, beryllium ion; $Cd^{+2}$, cadmium ion; $Mg^{+2}$, magnesium ion; $Cu^{+2}$, copper (II) ion; $Ca^{+2}$, calcium ion; $Ni^{+2}$, nickel (II) ion; $Pb^{+2}$, lead (II) ion; $Sn^{+2}$, tin (II) ion; $Hg^{+2}$, mercury (II) ion; $Co^{+2}$, cobalt (II) ion; $Fe^{+2}$, iron ion (II); $Mn^{+2}$, manganese ion (II); $Ba^{+2}$, barium ion; $Sr^{+2}$, strontium ion; $Cr^{+2}$, chromium (II) ion; $Sr^{+2}$, strontium ion; $Ra^{+2}$, Radio ion.

The term cell migration factor antagonist refers to those natural or synthetic compounds that inhibit cell migration. Illustrative, non-limiting examples of cell migration factor antagonists include, but are not limited to ISO-1, ISO-66, ISO-92 p425, K664-1, K-647, K-679, K-680, K-664.1, OXIM-11, D-T4, T-614 or Iguratimod.

The term "approximately" refers to a variability of ±10%.

The term commercial biopreservation solution (CBS), refers to a solution capable of preserving cells at a temperature of 2 to 8° C. Illustrative non-limiting examples of commercial biopreservation solution include, but are not limited to HypoThermosol-FRS, FGM (mean), Normosol-R, Plasma-Lyte, AQIX, Celsior, Viaspan.

The term cryopreservant refers to a solution capable of mitigating molecular stress generated by the change in temperature both in the process of freezing and thawing of cells. Illustrative non-limiting examples of commercial biopreservation solution include Cryostore CS2, Cryostore CS5, Cryostore CS10, ProFreeze, Aedesta, Cellvation, Cell Guardian, Synth-aFreeze Recovery, Sigma Freeze, FGM+5% DMSO.

In particular, this invention relates to the use of pterostilbene, which is an antioxidant of the stilbenes family and a resveratrol analog, in serum free/animal component free culture media (Serum Free/Xeno free; SF/XF, for cell expansion, such as dendritic cells, T lymphocytes (modified or unmodified), hematopoietic cells, T-regulatory cells (T-reg), mesenchymal stem cells (MSCs)), pluripotent stem cells and/or other stem cells (SCs) and/or other types of cells other than stem cells.

In particular, the pterostilbene molecule provides enriched SF/XF conditions for the expansion of different stem cells and/or other cell types, and this molecule also be used for the production of extracellular vesicles (EVs), including exosomes secreted by different cell types and that can be purified free of contaminating vesicles from other sources such as serum of animal or human origin. In particular, it provides SF/XF solutions for cryopreservation and/or biopreservation for short, medium, and long-term storage of clinical-grade cell therapy (CT) products. In particular, the invention demonstrates that exposure of Pterostilbene in combination with growth factors and/or carrier proteins and/or hormones and/or excipients, are suitable for the manufacture of clinical grade cell therapy products. In particular, the pterostilbene molecule can also be used as a pre-treatment of cells to improve its resistance to highly oxidative environments, these cells can be dendritic cells, T lymphocytes (modified or unmodified), hematopoietic cells, T-regulatory cells (T-reg), mesenchymal stem cells (MSCs), pluripotent stem cells and/or other stem cells (SCs) and/or other types of cells other than stem cells.

Surprisingly, the inventors have found that the presence of pterostilbene and/or a migration inhibitory factor antagonist optionally in combination with a bivalent cation, in the media and/or solutions of the invention improve both cell expansion and cell viability. after cryopreservation or biopreservation processes. Furthermore, the potentiating effect of pterostilbene in the culture medium is so effective that it allows obtaining good results in cell cultures in media free of animal serum (serum free) and even in media completely free of xenogeneic agents (xeno free), avoiding this way any animal contamination in the crops, improving the quality of the final product. Therefore, cells cultured and preserved according to the means and methods of the invention have the advantage of being clinically grade for therapeutic procedures, without requiring any additional processing.

This unexpected effect on cell viability and expansion even reduces the use of other usual supplements in animal cell cultures, especially human cells, such as platelet lysate. Thus, the invention makes it possible to significantly improve the manufacture of products for therapy based on human cells in practically all the methods associated with this type of therapy.

Thus, the applications of the medium, medium supplement or solution of the invention are related to:

i. Use as a stimulant to enhance cell expansion in mammalian cell culture, such as dendritic cells, CAR-T cells, T-reg cells, mesenchymal stem cells (MSCs), T lymphocytes, hematopoietic stem cells (HSC), stem cells pluripotent and/or other stem cells (CS) and/or other cell types different from stem cells.

ii. The use in a formulation of a serum free/xeno free culture medium for the small and large scale expansion of MSCs and other SCs, for the manufacture of cellular products and their application in cellular therapy.

iii. Use in the production of extracellular vesicles (EVs) including exosomes secreted by stem cells or any other cell type under conditions free of animal derived components and without metabolic restriction during cell culture.

iv. The use in the formulation of clinical grade solutions for cryopreservation or biopreservation, maintaining high levels of viability and functionality of products for cell therapy.

v. Use as a pretreatment for cells that will be subjected to highly oxidative environments.

It is evident to the person skilled in the art that the culture media for animal cells, especially for human cells, and more especially for human cells for cellular therapies, such as stem cells or others, require complex culture or preservation media, which include nutrients, buffer, growth factors, to indicate the most important. The addition of the medium, medium supplement or solution of the invention in these media always makes it possible to improve the expansion and preservation results of the cells, even dispensing with or reducing the usual components of these media, such as fetal bovine serum, platelet lysate. The advantage of eliminating these components would be to avoid contamination, especially with FBS vesicles, and the advantage of reducing platelet lysate significantly reduces culture costs.

The basis for the serum free/xeno free culture medium is a combination of major growth factors such as: TGFb and bFGF, carriers of molecules (Insulin, transferrin and selenic acid), antioxidants and cortisol, this basal formula is applied to cultivate SCs or other cell types for the production of EVs and exosomes, while supplementation of the basal formula with a low percentage (2%) of human platelet lysate is applied for cell expansion of autologous or allogeneic grade MSCs/SCs clinical with potential use in clinical trials and marketing. Both culture media are supplemented with the medium or medium supplement of the invention.

The evidences on the invention show that the MSC derived from the umbilical cord (UC) cultivated in conditions without serum with cells cultured with the culture medium of the invention with different concentrations of pterostilbene and with supplement of hPL to 2%, increased their cell population compared to control (basal medium, 10% FBS). UC derived MSCs exposed to this medium maintain their morphological characteristics (Examples 1 and 2; FIGS. 1A-D and FIGS. 2A-B).

Figure 2A:
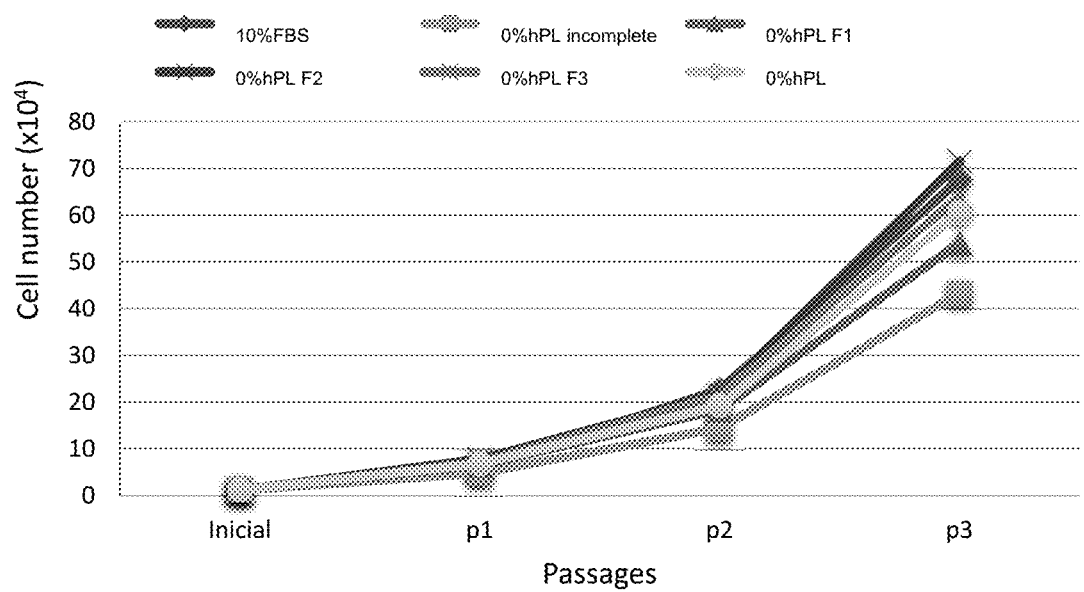
FIGS. 2A-B. Expansion of MSC in culture medium of the invention SF/XF.
Figure 2B:
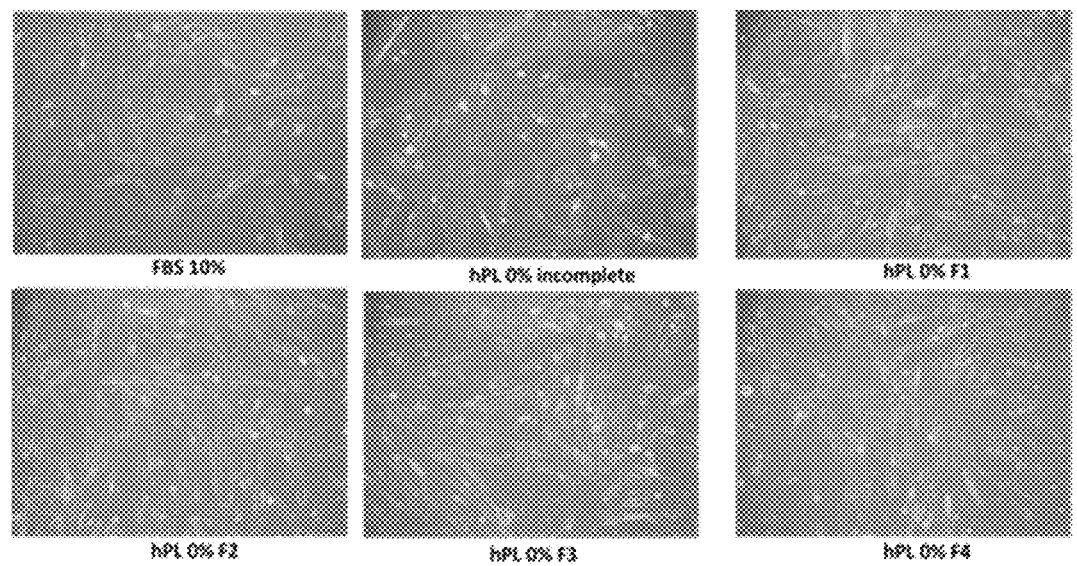

Meanwhile, the same cell source cultured with the basal form of the medium of the invention, without supplementing hPL, the same number of cells is obtained and with the same characteristics as in the control condition (FIG. 2A). Finally, it was observed that the cells maintained a fibroblast-like morphology, typical of MSC (FIG. 2B). All experiments were performed during passage 3, separating the cells every 5 days. In this case, the culture medium of the invention does not require any supplement of animal origin, and is appropriate for the manufacture of clinical grade cell products, and at the same time for the cultivation of MSC and other cell types, avoiding induction by starvation of cell culture for production of EV and exosomes.

As can be seen in the following aspects of the invention, the solution of the invention is especially useful for the biopreservation of cells. The evaluation of parameters such as survival, adhesion, proliferation and cell migration after the biopreservation process for 3 days, are improved with the use of the solution of the invention.

The inventors have shown that the cryopreservation solution of the invention improves conditions of cell viability and adherence, with respect to a widely used cryopreservative solution.

The inventors have shown that treatment of cells with the medium or medium supplement of the invention, and especially in embodiments comprising pterostilbene, against oxidative stress improves the survival of treated cells.

Thus, the invention relates to a composition for the cultivation, expansion, preservation and/or pretreatment of cells, in which said composition is a medium or supplement of medium or a solution comprising: (a) pterostilbene or its derivatives to a concentration between 10 µM to 100 µM, and/or (b) a migration inhibitory factor antagonist in a concentration between 0.01 nM to 1 nM, and optionally a bivalent cation in a concentration between 0.1 µM to 10 µM. Where the medium or medium supplement is free of serum and free of animal components. The migration inhibitory factor antagonist is chosen from ISO-1, ISO-66, ISO-92 p425, K664-1, K-647, K-679, K-680, K-664.1, OXIM-11, D-T4, T-614 or Iguratimod. On the other hand, the bivalent cation is chosen from zinc ion ($Zn^{+2}$, beryllium ion ($Be^{+2}$), cadmium ion ($Cd^{+2}$), magnesium ion ($Mg^{+2}$), copper (II) ion (cupric, $Cu^{+2}$), calcium ion ($Ca^{+2}$), nickel (II) ion (nickel, $Ni^{+2}$), lead (II) ion (plumbose, $Pb^{+2}$), (II) tin ion (stannous, $Sn^{+2}$), mercury ion (II) (mercuric, $Hg^{+2}$), cobalt (II) ion (cobalt, $Co^{+2}$), iron (II) ion (ferrous, $Fe^{+2}$), manganese (II) ion (manganous, $Mn^{+2}$), barium ion ($Ba^{+2}$), strontium ion ($Sr^{+2}$), chromium (II) ion ($Cr^{+2}$), strontium ion ($Sr^{+2}$), radio ion ($Ra^{+2}$). Additionally, the medium or medium supplement is for cell culture and/or expansion and comprises a basal medium with growth factors, hormones, amino acids, vitamins, inorganic salts and carbohydrates.

In one embodiment the medium or medium supplement is for cell culture and/or expansion, where the pterostilbene is in a concentration range of 100 nM to 1000 nM and comprises human platelet lysate in a proportion less than 10% of the culture, or less than 5% of the culture medium.

In another embodiment the medium or medium supplement is for production of extracellular vesicles (EV) including exosomes secreted by stem cells or any other cell type under conditions free of animal derived components without induction by starvation of cell culture and without use of human lysate platelets.

In another embodiment the composition of solutions of the invention for cell preservation, especially for bio-preservation and cryopreservation, where a solution of the invention comprises a cellular bio-preservation solution (CBS) and Pterostilbene in a concentration range of 10 nM at 10 μM. Where the solution is for biopreservation and comprises a biopreservative medium (CBS), Pterostilbene in a concentration range of 10 nM to 10 μM and Zinc in a concentration range of 0.1 μM to 10 μM. Where a solution is used for biopreservation and comprises a biopreservative medium (CBS), ISO-1 in a concentration range of 0.01 nM to 1 nM and Zinc in a concentration range of 0.1 μM to 10 μM. Additionally the solution is used for biopreservation and comprises a medium with biopreservative (CBS), Pterostilbene in a concentration range of 10 nM to 10 μM, ISO-1 in a concentration range of 0.01 nM to 1 nM and Zinc in a range concentration from 0.1 μM to 10 μM.

In another embodiment the composition of solutions of the invention for cell preservation, especially for bio-preservation and cryopreservation, where a solution of the invention comprises a solution for cryopreservation. Where the solution for cryopreservation comprises a solution with human platelets, cryoprotectant and pterostilbene in a concentration range of 200 nM to 20 μM and heparin in concentrations less than 5 units, every 500,000 cells.

In another embodiment the medium or medium supplement is for the pretreatment of cells that will be subjected to oxidative stress and comprises pterostilbene in a concentration range of 5 to 100 μM.

In another aspect the invention relates to a method for the culture, expansion, preservation and/or pretreatment of cells where cells are grown, expanded, preserved or pretreated in contact with a composition which is a culture medium, a supplement of medium or solution comprising: (a) pterostilbene or its derivatives at a concentration between 10 μM to 100 μM, and/or (b) a migration inhibitory factor antagonist at a concentration between 0.01 nM to 1 nM, and optionally a bivalent cation in a concentration between 0.1 μM to 10 μM.

Where cells are chosen from mesenchymal stem cells, iPSC, pluripotent stem cells, human embryonic stem cells, progenitor cells, CAR-T cells, regulatory T cells or dendritic cells. And the culture is carried out in a medium free of serum and free of animal components.

In one embodiment the cells are cultured and additionally the supernatant is separated from this culture, the supernatant is subjected to a purification process to obtain extracellular vesicles and/or exosomes from the cultured cells free of animal derived components (serum free and xeno free). In another embodiment, the cells are preserved, especially bio-preserved and cryopreserved. And in another embodiment the cells are pre-treated to withstand situations of oxidative stress and comprise contacting them with pterostilbene in a concentration range of 5 to 100 μM.

A first aspect of the invention relates to a culture medium or a medium supplement, hereinafter the culture medium of the invention, comprising:
 a) pterostilbene,
 b) growth factors,
 c) a hormone such as cortisol,
 d) enriched basal medium that promotes the growth of mammalian cells and comprises four basic chemical groups: amino acids, vitamins, inorganic salts, carbohydrates and other compounds.
 e) supplement composed of insulin, transferrin and selenosic acid (ITS).
 f) optionally human platelet lysate (hPL), depending on the application.

Preferably, the culture medium, medium supplement, and solutions of the invention are manufactured in compliance with Good Manufacturing Practice (GMP).

Culture Medium with Pterostilbene and Low hPL

The results described in Example 1 show that pterostilbene enrichment of a basal medium allows the cultivation of MCS without fetal bovine serum (FBS) with a very low percentage of human platelet lysate, thus obtaining a culture medium free of animal serum.

In a preferred embodiment of the invention, the culture medium of the invention is a serum free/xenogenic agent free culture medium, hereinafter the culture medium of the invention, wherein the basal medium comprises a mixture of Dulbecco's Modified Eagle's Medium (DMEM) without glucose and nutrient mixture of Ham's F12 (DMEM/F12), IT solution, bFGF, TGF-β, cortisol, pterostilbene and human platelet lysate.

In a preferred embodiment, the basal medium of the culture medium of the invention is prepared by mixing 50% by volume for each medium (Dulbecco's Modified Eagle's Medium (DMEM) and Ham's F12 Nutrient Mixture).

In another preferred embodiment, the culture medium of the invention or any of the other media defined in the first aspect, further comprises a mixture of human insulin, human transferrin, and selenesic acid (such mixture is commercially called "ITS"), and more preferably said ITS, preferably comprises recombinant human insulin, preferably recombinant human transferrin and preferably selenesic acid. Preferably the ITS solution is in a concentration range between 0.5× to 5×, more preferably in a concentration of 1×. Preferably insulin is in a concentration range of about 5 mg/L to about 50 mg/L, and more preferably of about 20 mg/L, preferably recombinant human transferrin, and more preferably, said transferrin is in a concentration range of about 150 mg/L to about 750 mg/L, and more preferably about 550 mg/L, preferably selenosic acid, and more preferably, said selenesic acid is in a concentration range of from about 0.30 mg/L to about 0.80 mg/L, and more preferably from about 0.70 mg/L.

In another preferred embodiment, the culture medium or any of the other media defined in the first aspect, further comprises Basic Fibroblast Growth Factor (bFGF), more preferably Recombinant Basic Human Fibroblast Growth Factor, and more preferably said bFGF is in a concentration range from about 1 μg/L to about 75 μg/L, and more preferably from about 25 μg/L.

In another preferred embodiment, the culture medium, or any of the other media defined in the first aspect, further comprises transforming growth factor (TGF-β), more preferably recombinant transforming growth factor β (TGF-β), and more preferably said TGF-β is in a concentration range of from about 0.5 μg/L to about 5 μg/L, and more preferably from about 2 μg/L.

In another preferred embodiment, the serum-free culture medium or any of the other media defined in the first aspect, further comprises cortisol, and more preferably, said cortisol is in a concentration range of from about 1 nM to about 100 nM and more preferably about 50 nM.

In another preferred embodiment, the pterostilbene is in a concentration range from about 100 μM to about 100 μM, more preferably it is in a concentration range from about 0.001 μM to 10 μM. Even more preferably the pterostilbene is at 5 μM.

In a preferred embodiment of the invention, the culture medium of the invention is only supplemented with human platelet lysate in an amount less than 10%, preferably less than 7.5%, more preferably less than 5%, volume/volume of total culture medium.

In another preferred embodiment, said culture medium is used for cell expansion, both in monolayer and suspension cultures. Example 1 describes the method and use of the culture medium for the cell culture and expansion of mesenchymal stem cells from the umbilical cord, it is observed that the medium of the invention serves for optimal cell growth, without observing a loss of own characteristics of the cells.

Culture Medium with Pterostilbene

The results described in Example 2 show that the pterostilbene enrichment of a basal medium allows the cultivation of MCS without fetal bovine serum (FBS), maintaining cell growth and allowing cell products such as extracellular vesicles to be obtained, free of animal components.

In a preferred embodiment of the invention, the culture medium of the invention is a serum free/animal component free culture medium, hereinafter the SF/XF culture medium of the invention, wherein the basal medium it comprises a mixture of Dulbecco's modified Eagle's medium (DMEM) without glucose and nutrient mixture of Ham's F12 (DMEM/F12), ITS solution, bFGF, TGF-β, cortisol, pterostilbene and human platelet lysate.

In a preferred embodiment, the basal medium of the culture medium of the invention is prepared by mixing 50% by volume for each medium (Dulbecco's Modified Eagle's Medium (DMEM) and Ham's F12 Nutrient Mixture).

In another preferred embodiment, the culture medium of the invention or any of the other media defined in the first aspect, further comprises a mixture of human insulin, human transferrin, and selenesic acid (such mixture is commercially called "ITS"), and more preferably said ITS, preferably comprises recombinant human insulin, preferably recombinant human transferrin and preferably selenesic acid. Preferably the ITS solution is in a concentration range between 0.5× to 5×, more preferably in a concentration of 1×. Preferably insulin is in a concentration range of about 5 mg/L to about 50 mg/L, and more preferably of about 20 mg/L, preferably recombinant human transferrin, and more preferably, said transferrin is in a concentration range of about 150 mg/L to about 750 mg/L, and more preferably about 550 mg/L, preferably selenosic acid, and more preferably, said selenosic acid is in a concentration range of about 0.30 mg/L to about 0.80 mg/L, and more preferably about 0.70 mg/L.

In another preferred embodiment, the culture medium, or any of the other media defined in the first aspect, further comprises Basic Fibroblast Growth Factor (bFGF), more preferably Recombinant Basic Human Fibroblast Growth Factor, and more preferably said Basic Fibroblast Growth Factor is in a concentration range from about 1 μg/L to about 75 μg/L, and more preferably from about 25 μg/L.

In another preferred embodiment, the culture medium, or any of the other media defined in the first aspect, further comprises transformation growth factor (TGF-β), more preferably recombinant transformation growth factor (TGF-β), and more preferably, said Transformation Growth Factor (TGF-β) is in a concentration range from about 0.5 μg/L to about 5 μg/L, and more preferably from about 2 μg/L.

In another preferred embodiment, the serum-free culture medium or any of the other media defined in the first aspect, further comprises cortisol, and more preferably, said cortisol is in a concentration range of from about 1 nM to about 100 nM and more preferably about 50 nM.

In another preferred embodiment, pterostilbene is in a concentration range of from about 100 μM to about 100 μM, more preferably it is in a concentration range of about 0.001 μM to 10 μM. Even more preferably, pterostilbene is at approximately 5 μM.

In another preferred embodiment, said culture medium is used for cell expansion, both in monolayer and suspension cultures, and to obtain extracellular products such as microvesicles. Example 2 describes the method and use of the culture medium for cell culture and expansion of mesenchymal stem cells from the umbilical cord, it is observed that the medium of the invention serves for optimal cell growth, without observing a loss of own characteristics of the cells. In addition, the obtaining of microvesicles is described, such as obtaining complete exosomes, which are evaluated by obtaining the number of total particles and particles less than 150 nm from the culture.

Cell culture of stem cells and other cell types for the production of EV and exosomes under SF/XF conditions.

In another embodiment, the invention relates to production and purification of secreted EVs including exosomes isolated from mammalian cell types, preferably stem cells, more preferably MSCs cultured using the culture medium of the invention for cell expansion.

In another preferred embodiment, the secreted EVs include exosomes isolated from different cellular sources.

In another preferred embodiment, the EV and/or Exosome production process comprises: adhesion of the cells to plastic surfaces in 2D (plates or culture flasks) or 3D (microcarriers or macrocarriers), washing of the basal medium, growth of the cells adhered, obtaining continuous supernatant and purification of EVs and/or Exosomes.

In another preferred embodiment, for adhesion of the 3D surface cells, said cells must be seeded at a rate of approximately 4 million cells per 1 g of Bionoc. Understanding the term "approximately" to a variation of 10 percent.

In another preferred embodiment, for adhesion of the cells to the 3D surfaces, it is performed in the presence of a basal medium solution composed of DMEM with 10% FBS. In another preferred embodiment, for adhesion of the cells to the 3D surfaces, the cells should be left with the mentioned medium under gentle agitation and with temperature control for approximately 24 hours. Understanding the term "approximately" to a variation of 10 percent.

In another preferred embodiment, for washing the basal medium, after the cells are attached, they must be washed with SF/XF culture medium solution of the invention at least 2 times. After washing, the SF/XF culture medium solution of the invention is added again for cell growth with gentle agitation and with temperature control for at least 3 days.

In another preferred embodiment, to continuously obtain EVs and/or exosomes from the cell culture supernatant, when the confluence of the cells reaches at least 80%, the supernatant is collected. For cell culture maintenance by producing EVs and/or Exosomes, SF/XF culture medium of the invention must be added in the same proportion to the volume extracted from the supernatant. This procedure can be done continuously.

In another preferred embodiment, the purification of EVs and/or Exosomes from the obtained supernatant is carried out in different steps: centrifugation, filtration, ultracentrifugation, washing and resuspension. Preferably, the supernatant should be centrifuged at 600 g for 10 minutes at approximately 4° C. To be subsequently filtered using 0.22 um PES filter units. To subsequently subject the samples to ultra-centrifugation at 100,000 g for 70 minutes at approximately 4° C. Subsequently, once the EVs and/or exosomes have been centrifuged and concentrated, the supernatant is removed and stored with PBS at 4° C. overnight (washing). Once the washing stage is completed, the pellet is resuspended in PBS and aliquoted and finally stored at −80° C.

EVs are extracellular particles that vary in size as they range from 40 to 1000 nm. On the other hand, exosomes are characterized by their rounded shape and by their size ranging from 30-200 nm, preferably from 30-150 nm, more preferably from 50-100 nm, and by the expression of the HSP90, HSP70 and CD63 markers. It should be noted that by using the SF/XF culture medium of the invention, it is not necessary to subject the cells to periods of caloric restriction (traditionally called "induction") that alter the metabolism of the cell and therefore the quality of the exosomes. (FIGS. 3A-B), allowing the collection of exosomes constantly and periodically and in free conditions of components of animal origin, by the techniques known in the art.

Cryopreservation and biopreservation of clinical grade cell therapy products. In another aspect of the invention, the elements of the invention are used for a cell preservation solution. In a preferred embodiment a solution of the invention is an additive for biopreservation. In another preferred embodiment a solution of the invention is for cell preservation, specifically cell bio-preservation and cryopreservation.

In a preferred embodiment, the solution comprises pterostilbene, a migration inhibiting factor antagonist, and a bivalent cation in combination or separately, to be used as an additive to commercial biopreservation solutions.

In a preferred embodiment, pterostilbene is in a concentration range from about 0.00001 µM to 100 µM, more preferably in a concentration range from about 0.05 µM to 1 µM, and even more preferably to about 0.1 µM.

In a preferred embodiment, the antagonist of the migration inhibitory factor corresponds to ISO-1, more preferably it is in a concentration range of approximately 0.000001 µM to 0.001 µM, more preferably in a concentration range of approximately 0.000005 µM to 0.0005 µM, and even more preferably at about 0.0001 µM.

In a preferred embodiment, the bivalent cation corresponds to Zinc, more preferably it is in a concentration range of about 0.025 µM to 250 µM, more preferably in a concentration range of about 0.25 µM to 25 µM, and even more preferably at about 2.5 µM.

In another preferred embodiment, the cryopreservant solution is composed of human platelet lysate, heparin, a cryoprotectant solution, and Pterostilbene. More preferably, the human platelet lysate is in a concentration range of about 90% to about 99%, more preferably at a concentration of 95%. Heparin is preferably in a concentration range of between 1 IU/mL-10 IU/mL, and even more preferably it is in a concentration of 2 IU/mL. The cryoprotectant solution is preferably dimethyl sulfoxide, preferably is in a concentration range of between 1%-10%, and even more preferably is in a concentration of 5%. Pterostilbene is preferably in the range of 0.5 µM to 10 µM, and even more preferably at a concentration of 2 µM.

Pretreatment for cells that will besubjected to highly oxidative environments. In a third aspect of the invention, pterostilbene is used as a pre-treatment for different cell types in the prevention of situations that cause oxidative stress.

In a preferred embodiment the cells are cultured with basal medium and pterostilbene for a time before exposure to oxidative stress. Preferably pterostilbene is in a concentration range of about 0.5 µM and about 100 µM, more preferably at a concentration of 10-50 µM. Preferably, the cultivation time is in a range of about 1 hour to 300 hours, more preferably between 1 hour and about 72 hours.

The invention will be more clearly perceived and better understood from the following specific examples which are intended to provide examples of certain preferred embodiments and which do not limit the scope of the present invention.

EXAMPLES

Example 1: Expansion of MSC in Culture Medium of the Invention with hPL

Mesenchymal stem cells derived from the umbilical cord were expanded with the medium of the invention from passage 0 to passage 3, where the basal media used were Dulbecco's modified Eagle's medium (DMEM) without glucose and the mixture of nutrients F12 from Ham (DMEM/F12) supplemented with 25 µg/L bFGF, 2 µg/L TGFβ and 2% human platelet lysate (hPL) and pterostilbene at different concentrations; 0 nM pterostilbene (f0), 100 nM pterostilbene (F1); 250 nM pterostilbene (F2); 500 nM pterostilbene (F3) and 1000 nM pterostilbene (F4). The control situation corresponds to the use of basal media with 10% FBS. All the experiments were carried out by 3 passages, dividing the cells every 5 days. After the experiments, the number of cells was measured by the trypan blue exclusion test.

Figure 1B:
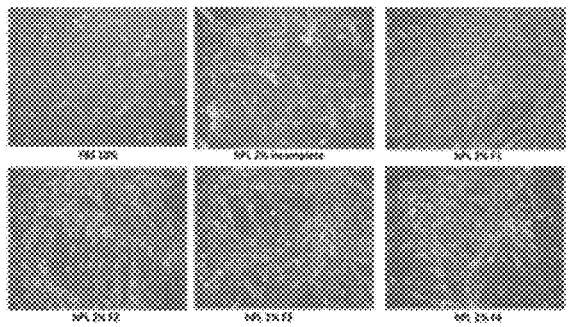
Figure 1C:
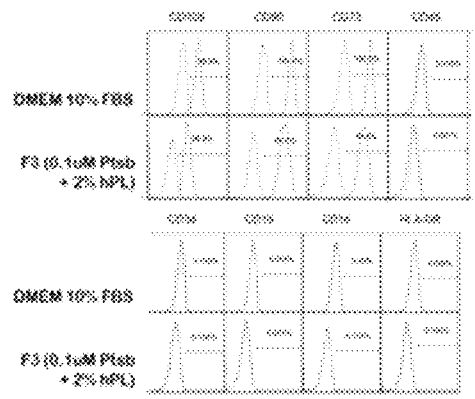
Figure 1D:
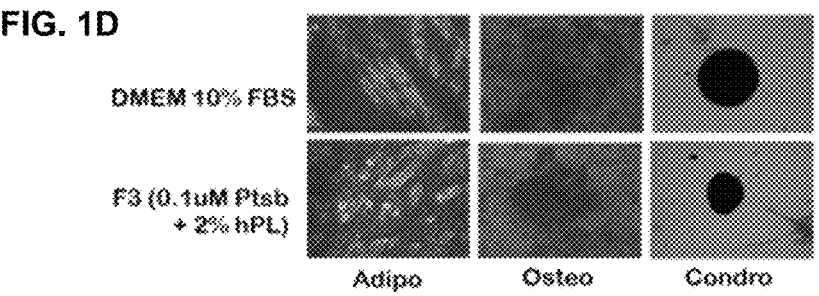

As clearly seen in FIG. 1A, after the 3 passages, the medium with the worst cell expansion was the condition with only 2% hPL, without addition of Pterostilbene. Surprisingly, the second condition with the least expansion was the medium with 10% FBS, which is the standard average for international cell expansion. All the conditions of the invention obtain better results, and the best result was 2% hPL and 500 nM pterostilbene (F3), achieving almost 200,000 more cells than the FBS media. FIG. 1B shows images of the cultures at the end of the experiments, in all the tests the morphological characteristics of the MSCs derived from the umbilical cord are maintained. Furthermore, cells cultured after three passages maintain the MSC phenotype, (FIG. 1C), as well as the potential for differentiation (FIG. 1D).

Example 2: Expansion of MSC in Culture Medium of the SF/XF Invention

Umbilical cord derived mesenchymal stem cells expanded under 6 different conditions, where the basal media used were Dulbecco's Modified Eagle's Medium (DMEM) without glucose and Ham's F12 Nutrient Mix (DMEM/F12) supplemented with 25 µg/L bFGF, 2 µg/L TGF-β. Conditions were basal media plus: 10% FBS; 0% human platelet lysate (hPL) (incomplete); 0% hPL and 100 nM pterostilbene (F1); 0% hPL and 250 nM pterostilbene (F2); 0% hPL and 500 nM pterostilbene (F3) and 0% hPL and 1000 nM pterostilbene (F4). All experiments were carried out in 3 passages, harvesting the cells every 5 days. After the experiments, the number of cells was measured by the trypan blue exclusion test. The results are shown in FIG. 2A. After 3 passages, the medium with the worst cell expansion was the 0% hPL condition, that is, the basal medium only. Basal media supplemented with Pterostilbene only have better results, and condition F2 has better results than media with 10% FBS. FIG. 2B shows images of the cultures at the end of the experiments, in all the tests the morphological characteristics of the UC-derived MSCs are maintained.

Example 3: Cell Culture in Macrocarriers of Stem Cells and Other Cell Types for the Production of EV and Exosomes Under Conditions with Animal Components and Under SF/XF Conditions The commercial macrocarrier, called Bionoc II, was used, which is weighed under sterile conditions, under a hood, then the macrocarrier is subjected to a treatment with UV light for 30 minutes. Subsequently, the carriers were placed in a 300 ml Erlenmeyer flask, and the cells were seeded at a rate of 4 million cells/g.

For cell culture, cells were seeded in 50 ml of DMEM+10% FBS medium, for both experiments with the precaution that the carrier be completely covered with medium. The Erlenmeyer flasks are left in incubation with temperature and $CO_2$ control, without shaking Over Night (O.N.), so that the cells adhere to the carrier.

Subsequently, for the traditional exosome production medium, 150 ml of DMEM+10% FBS medium are added to the culture medium corresponding to each flask and are left in incubation with control of temperature and $CO_2$ and constant agitation of 20 rpm. On the other hand, for the production of exosomes with the SF/XF culture medium of the invention, all DMEM+10% FBS should be removed with 2 washes with PBS and proceed to add 150 ml of SF/culture medium XF of the invention to the culture. To determine if the cells are adhered to Bionoc II, a Hoechst stain (1:2000) is performed, incubated for 10 minutes and observed under a microscope.

The traditional method of producing exosomes from cell culture with DMEM requires alternation with culture media without animal supplements such as FBS or hPL, for which reason a "caloric restriction induction (starving)" is carried out, where it is exchanged for the same volume. DMEM+FBS medium, by DMEM without phenol red in order to induce the production of exosomes. The supernatant can be collected a couple of days after induction. If more supernatant is required to be collected, the induction must be repeated. For this example, the supernatants were removed on days 8 and 12 of the experiment, as seen in FIG. 3A.

Figures 3A, 3B:
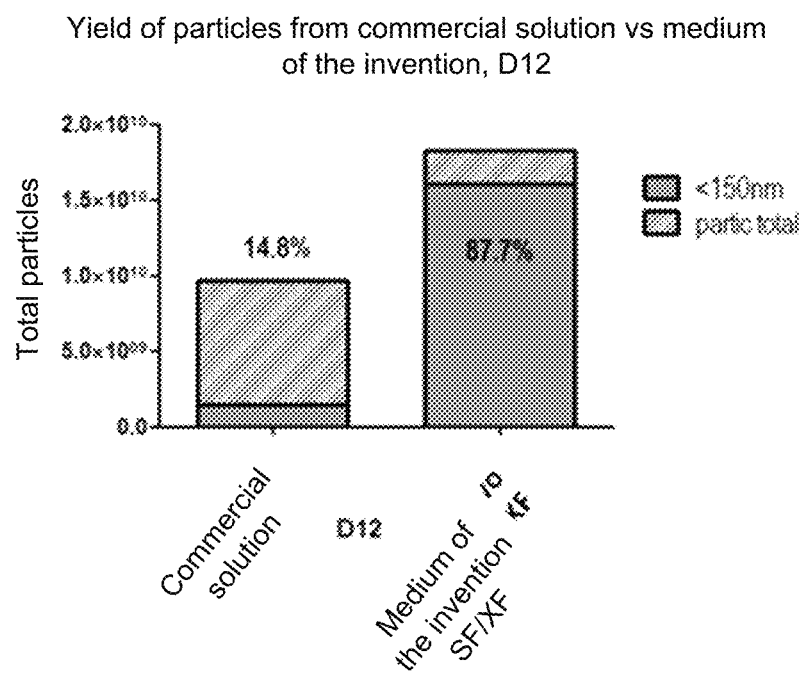
FIGS. 3A-B. Cell culture in macrocarriers of stem cells and other cell types for the production of EV and exosomes under conditions free of animal components and under SF/XF conditions.

On the other hand, cell culture with the SF/XF medium of the invention does not require induction by caloric restriction, therefore it allows a sustained production of extracellular vesicles without subjecting the cell to metabolic changes, therefore the sustained culture allows the enrichment of particles, especially those smaller than 150 nm, as can be seen in FIG. 3B.

From the cell culture with the SF/XF medium of the invention, the collection of the supernatant can be started in a sustained manner, in the example they were collected on days 5, 8 and 12, as observed in FIG. 3A. Each time supernatant was collected, the same volume was replaced with the culture medium of the invention.

The supernatant obtained from the cell cultures was centrifuged at 600 g for 10 minutes at 4° C. and subsequently filtered using 0.22 μm PES filter units. To then be frozen or processed directly in an ultracentrifuge.

The supernatants were ultracentrifuge processed at 100,000 g for 1 hour and 10 minutes at 4° C., this step was repeated until the total volume of the supernatant was processed. The supernatant was removed, and the pellets were released using a vortex. Subsequently, the pellets were subjected to two washes in order to eliminate possible contaminants. For this, the pellets were resuspended in filtered PBS reaching a final volume of 10 ml, and centrifuged at 100,000 g at 4° C. over night. Subsequently, the last wash was carried out, for which the supernatants were removed, and the pellets were resuspended in a final volume of 10 ml and were processed for 1 hour and 10 minutes of ultra-centrifuge at 100,000 g. Finally, the supernatant is removed, the pellets are passed through a vortex and can be aliquoted for storage.

Particle quantification was done using a dilution of the pellet in filtered PBS (1:100), using NanoSight NS300. This quantification shows that first the SF/XF medium of the invention manages to produce approximately 1.6 times more total particles than the traditional method. Second, the SF/XF medium of the invention manages to produce particles smaller than 150 nm in a ratio of 23 times more than the traditional way, on day 12.

Example 4: Biopreservation of Clinical Grade Cell Therapy Products

Figure 4A:
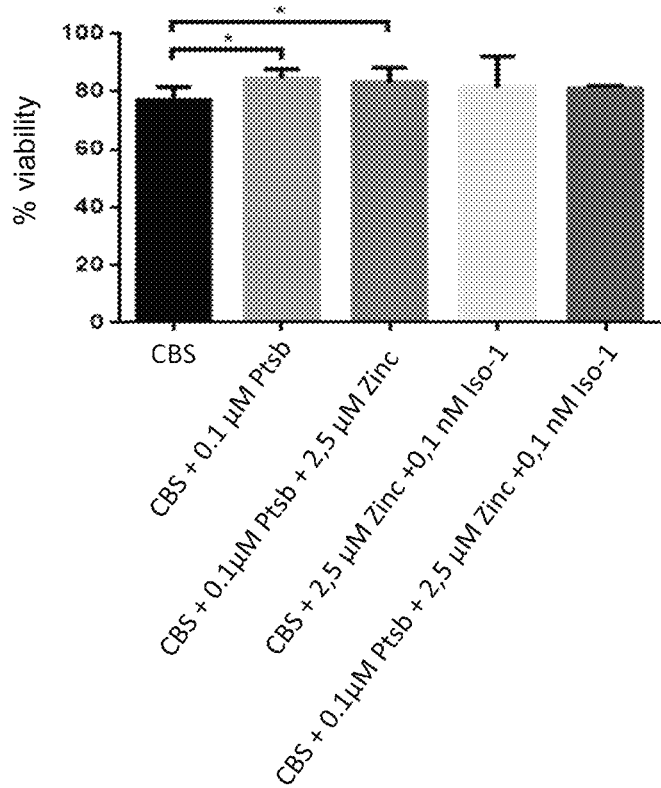
FIGS. 4A-D. Biopreservation of MSCs.
Figure 4B:
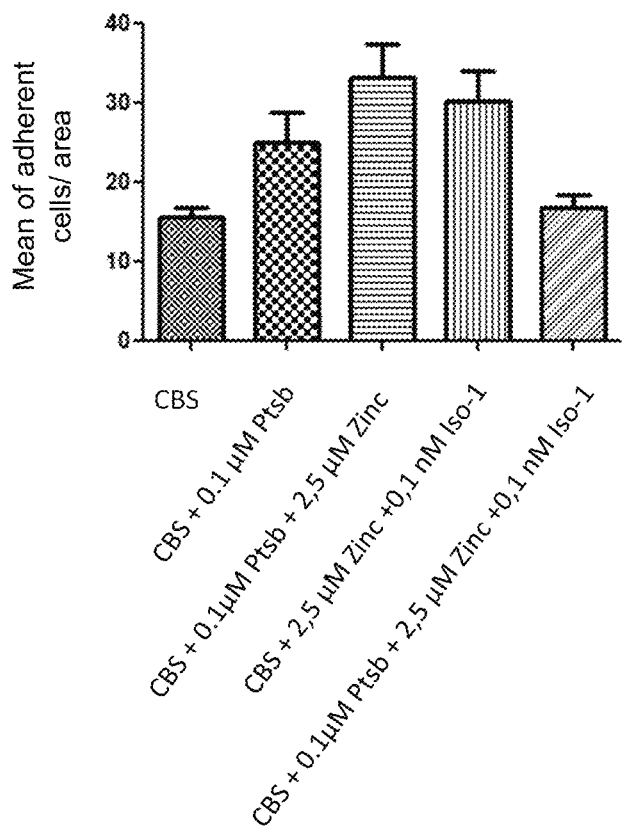
Figure 4C:
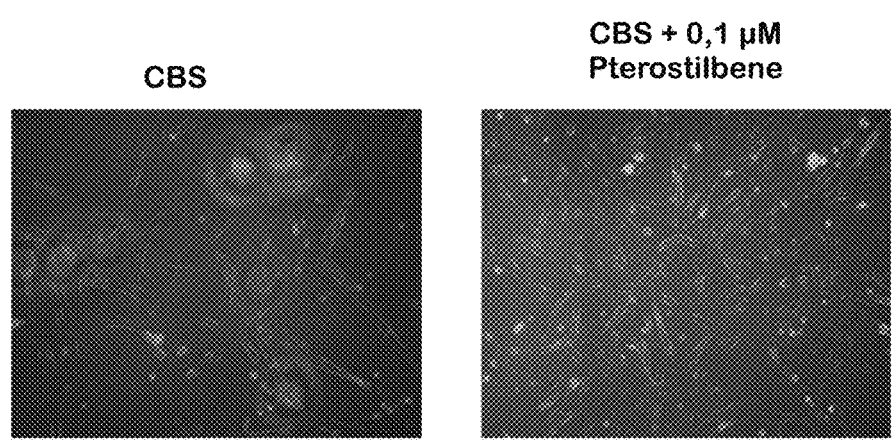
Figure 4D:
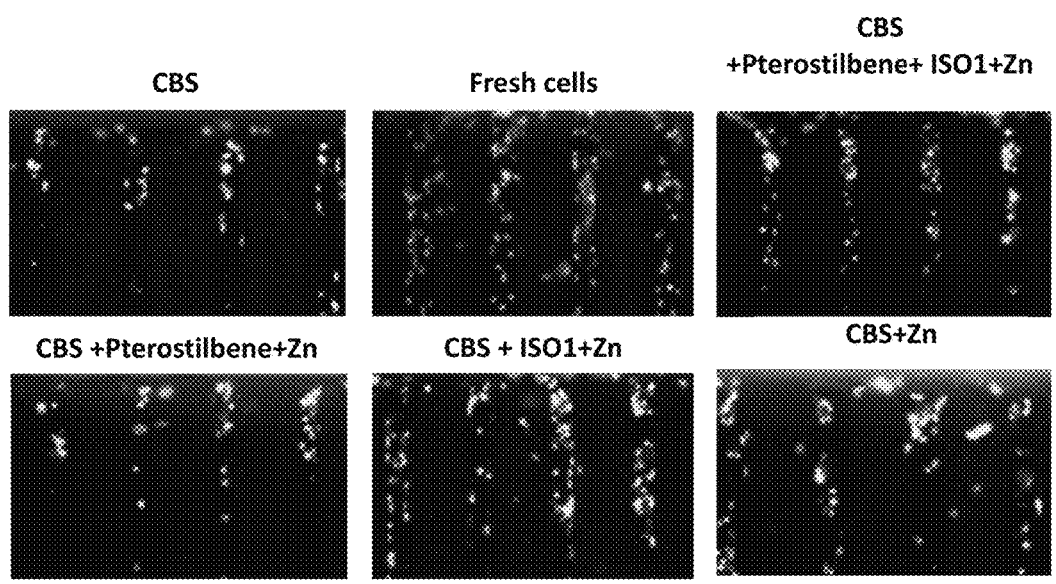

Approximately 200,000 umbilical cord derived mesenchymal stem cells were stored in 200 μl of commercial biopreservation solution (CBS) as a control and 200 μl of CBS supplemented with the medium supplement of the invention. The samples were kept at 4° C. for three days. Cells were resuspended in DMEM base, and viability was assessed by trypan blue exclusion assay. The CBS medium with the different supplements of the medium of the invention (pterostilbene, pterostilbene+$Zn^{+2}$, ISO-1+$Zn^{+2}$, pterostilbene+ISO-1+$Zn^{+2}$) gave a better cell viability, in the case of Pterostilbene 0.1 μM is approximately 10% better compared to CBS alone (P<0.01; t-test of student), FIG. 4A. Cell adhesion was evaluated 24 hours after cells were seeded in 10 mm plates. More cells adhered in the CBS condition were observed with the culture medium supplement (0.1 μM pterostilbene, 2.5 μM Zn and/or 0.1 nM ISO-1), compared to CBS alone (FIG. 4B), and more cells maintained their migration potential when those cells preserved with the supplement of the culture medium of the invention were evaluated with CBS against CBS (FIG. 4C). Finally, the cells preserved with CBS proliferated less than those preserved in CBS with pterostilbene (FIG. 4D). Therefore, the solution of the invention improves the functionality of the cells after 3 days of biopreservation.

Example 5: Cryopreservation of Clinical Grade Cell Therapy Products

Approximately 500,000 umbilical cord derived mesenchymal stem cells were stored in 500 μl of a human platelet based solution, 2.5 units of heparin, 5% DMSO and 2 μM Pterostilbene compared to a commercial cryopreservation solution and as a control 90% fetal bovine serum (FBS) and 10% DMSO were used. The samples were progressively frozen at 1° Celsius/min until they reached −80° C. and stored at that temperature for one day. The samples were immersed in liquid nitrogen (−196° C.) and were cryopreserved for more than 7 days.

Figure 5A:
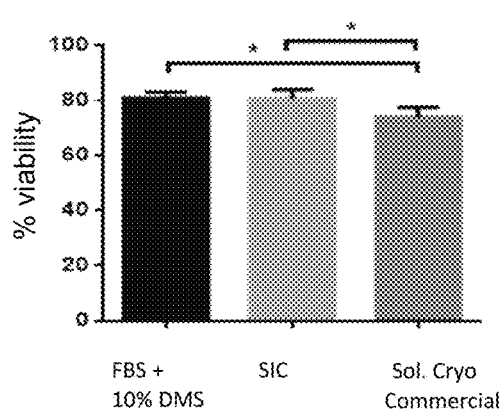
FIGS. 5A-C. Cell preservation using cryopreservation solution of the invention.
Figure 5B:
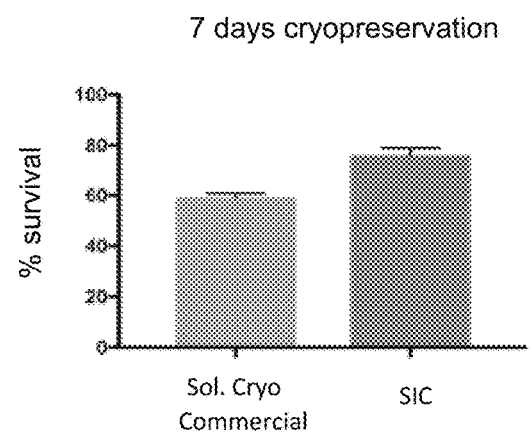
Figure 5C:
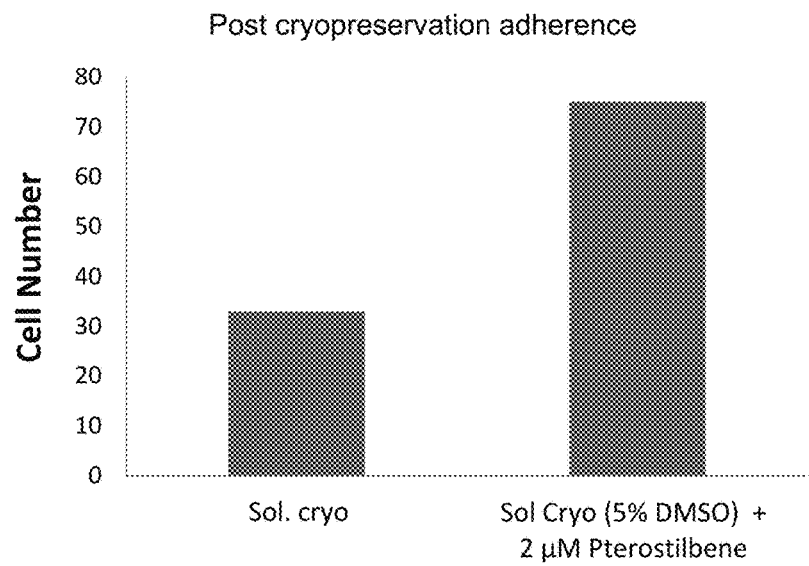

Subsequently, the samples were rapidly thawed and the medium for cryopreservation was removed by centrifugation. Cells were resuspended in DMEM base medium and viability was assessed by trypan blue exclusion assay. The results are shown in FIGS. 5A-C.

The cryopreservation solution with 2 uM of pterostilbene gave a similar viability to the conventional cryopreservation solution (control FBS+10% DMSO), with the advantage that this solution is XF and presents a 50% reduction in the composition of DMSO that to concentrations greater than 5% can be toxic to humans. Regarding the commercial solution, the viability percentage was significantly higher, by 7% (FIG. 5A). The net effect of pterostilbene is observed in FIG. 5B, where it can be seen that the pterostilbene-free human platelet-based cryopreservation solution has a viability percentage approximately 20% lower than the solution containing Pterostilbene (P<0.05 using Student's t-test). Cells were seeded and their morphology and adherence were evaluated for one week. Cells that were stored with Pterostilbene showed better adherence 24 hours after being sown compared to those that were not stored in this condition (FIG. 5C). Cells preserved with the cryopreservation culture medium of the invention also have a better migration capacity compared to those that were cryopreserved with another method.

Example 6: Preventive Antioxidant Effect of Pterostilbene in Cell Culture

Figure 6:
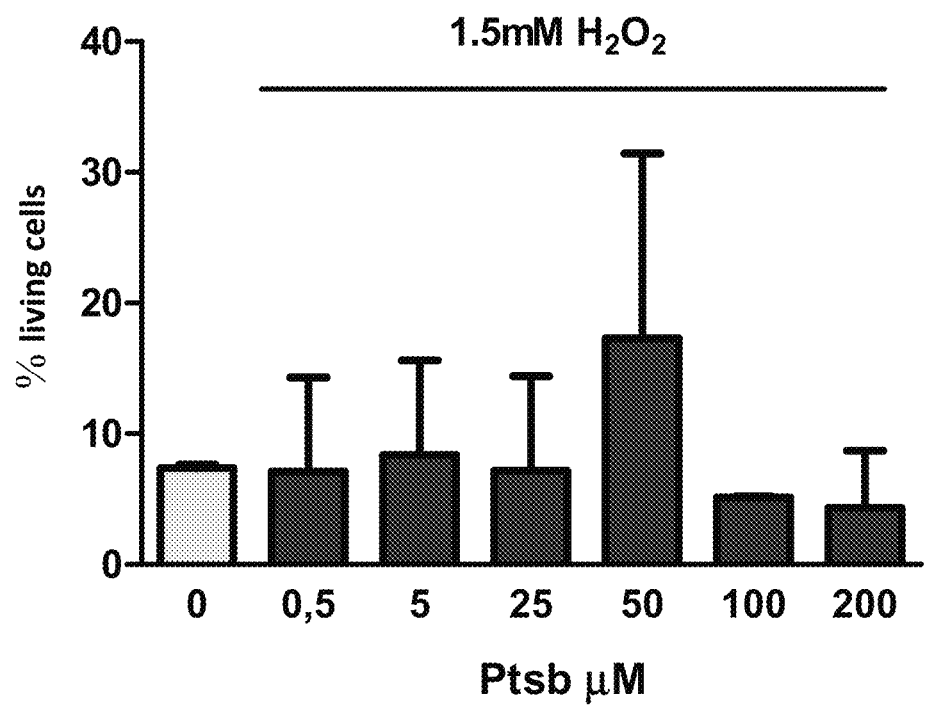
FIG. 6. Cells were cultured for 4 hours in the presence of different concentrations of Pterostilbene and subsequently subjected to oxidative stress by induction with H2O2. The graph shows the percentage of live cells (evaluated by Anexin V/7AAD) after induction with 1.5 mM H2O2, observing a resistance to stress at 50 µM of Pterostilbene. Ptsb: Pterostilbene.

Mesenchymal stem cells obtained from the umbilical cord, which were in passage 4, were cultured in the presence of pterostilbene as a pretreatment method against oxidative stress. 100,000 cells were seeded in each well, for 4 hours in the presence of different concentrations of Pterostilbene and subsequently subjected to oxidative stress by induction with 1.5 mM, $H_2O_2$. FIG. 6 presents a graph showing the percentage of living cells (Anexin V/7AAD) after induction with 1.5 mM $H_2O_2$, observing resistance to oxidative stress at 50 µM pterostilbene.

The examples described should be considered illustrative and not limiting, and demonstrate the advantages of the invention in all the aspects indicated for the manufacture of products for therapy based on human cells of the medium, supplement for medium and solution of the invention and the methods that employ, those which are protected in the appended claims.

The invention claimed is:

1. A composition for the culture, expansion, or preservation of cells, wherein the composition is a medium, supplement of medium, or solution comprising:
   pterostilbene at a concentration between 10 µM to 100 µM,
   basic fibroblast growth factor (bFGF) at a concentration between 1 µg/L to about 75 µg/L, and
   transforming growth factor beta (TGF-β) at a concentration between 0.5 µg/L to about 5 µg/L,
   wherein the composition is serum free.

2. The composition according to claim 1, wherein it is a medium, supplement of medium, or solution that is free of animal components (xeno free).

3. The composition according to claim 2, wherein it is a medium or medium supplement for the cultivation and/or expansion of cells and comprises a basal medium with growth factors, hormones, amino acids, vitamins, inorganic salts and carbohydrates.

4. The composition according to claim 3, wherein it is a medium or medium supplement for the production of extracellular vesicles (EV) including exosomes secreted by stem cells or any other cell type under conditions free of components derived from animals.

5. The composition according to claim 3, wherein it is a medium or medium supplement for culture and/or expansion of cells, where the pterostilbene is in a concentration range of 100 nM to 1000 nM and comprises lysate of human platelets in a proportion less than 10% of the culture medium.

6. The composition according to claim 5, wherein it comprises human platelet lysate in a proportion of less than 5% of the culture medium.

7. The composition according to claim 2, wherein it is a solution for the preservation of cells, especially for biopreservation and cryopreservation, and it comprises a cellular biopreservation solution (CBS) and Pterostilbene in a concentration range of 10 nM to 10 µM.

8. The composition according to claim 7, wherein the solution is for biopreservation and comprises a solution with biopreservant (CBS), and Pterostilbene in a concentration range from 10 nM to 10 µM, ISO-1 in a concentration range from 0.01 nM to 1 nM, or Zinc in a concentration range from 0.1 µM to 10 µM.

9. The composition according to claim 8, wherein the solution is used for cryopreservation and comprises a medium with human platelets, cryoprotectant and Pterostilbene in a concentration range of 200 nM to 20 µM and Heparin in concentrations less than 5 units/ml.

10. The composition according to claim 2, wherein the composition is a medium or medium supplement which is for the pre-treatment of cells that will be subjected to oxidative stress and includes pterostilbene in a range of concentration from 5 to 100 µM.

11. Method for the culture, expansion, and/or preservation of cells wherein cells are grown, expanded, or preserved in contact with a composition that is a medium, a medium supplement, or a solution comprising:
    pterostilbene at a concentration between 10 µM to 100 µM, and
    in a serum free medium or solution supplemented with Basic Fibroblast Growth Factor (bFGF) at a concentration between 1 µg/L to about 75 µg/L, and transforming growth factor (TGF-β) at a concentration between 0.5 µg/L to about 5 µg/L.

12. The method according to claim 11, wherein the cells are chosen between mesenchymal stem cells, iPSC, pluripotent stem cells, stem cells, human embryonic cells, progenitor cells, CAR-T cells, regulatory T cells or dendritic cells.

13. The method according to claim 11, wherein the culture is carried out in a medium free of animal components (xeno free).

14. The method according to claim 13 wherein the cells are cultured and additionally the supernatant is separated from this culture, the supernatant is subjected to a purification process to obtain extracellular vesicles and/or exosomes from cultured cells free of animal derived components (serum free and xeno free).

15. The method according to claim 11, wherein the cells are preserved.

16. The method according to claim 11, wherein the cells are cultured to withstand situations of oxidative stress and comprise contacting them with a composition comprising pterostilbene in a concentration range of 5 to 100 µM.

* * * * *